(12) United States Patent
Wynn et al.

(10) Patent No.: US 7,973,923 B2
(45) Date of Patent: Jul. 5, 2011

(54) MULTI-PORT INLINE FLOW CELL FOR USE IN MONITORING MULTIPLE PARAMETERS IN A SANITARY PROCESS LINE

(75) Inventors: William H. Wynn, Hillsborough, CA (US); Brian Patrick Costelloe, Costa Mesa, CA (US)

(73) Assignee: Endress+Hauser Conducta Inc., Anaheim, CA (US)

( * ) Notice: Subject to any disclaimer, the term of this patent is extended or adjusted under 35 U.S.C. 154(b) by 277 days.

(21) Appl. No.: 12/430,626

(22) Filed: Apr. 27, 2009

(65) Prior Publication Data

US 2010/0269940 A1 Oct. 28, 2010

(51) Int. Cl.
*G01N 1/00* (2006.01)
(52) U.S. Cl. ...................................................... 356/246
(58) Field of Classification Search ........... 356/244–246
See application file for complete search history.

(56) References Cited

U.S. PATENT DOCUMENTS

| | | | | |
|---|---|---|---|---|
| 4,076,420 | A | * | 2/1978 | De Maeyer et al. ............ 356/73 |
| 4,279,509 | A | * | 7/1981 | Daffern ......................... 356/246 |
| 4,284,412 | A | * | 8/1981 | Hansen et al. ............... 435/7.24 |
| 4,988,155 | A | | 1/1991 | Harner et al. |
| 5,078,493 | A | | 1/1992 | Evens et al. |
| 5,371,585 | A | * | 12/1994 | Morgan et al. ................ 356/246 |
| 5,407,638 | A | * | 4/1995 | Wang ......................... 422/82.09 |
| 5,452,082 | A | * | 9/1995 | Sanger et al. ................. 356/246 |
| 5,521,384 | A | | 5/1996 | Lynch |
| 5,905,271 | A | * | 5/1999 | Wynn ........................... 250/573 |
| 6,259,527 | B1 | | 7/2001 | Rahikkala et al. |
| 7,369,226 | B1 | * | 5/2008 | Hewitt .......................... 356/244 |
| 7,390,662 | B2 | * | 6/2008 | Riley et al. ...................... 436/10 |

* cited by examiner

*Primary Examiner* — Michael P Stafira
(74) *Attorney, Agent, or Firm* — Edward S. Wright

(57) ABSTRACT

Inline flow cell for use in monitoring multiple parameters in a sanitary process line, comprising a body with opposing end walls, a flow passageway extending along an axis between the end walls, and a plurality of side walls disposed tangentially about the axis, inlet and outlet fittings communicating with the passageway at the ends of the body for connecting the flow cell in a sanitary process line with fluid in the line flowing through the passageway, and monitoring ports opening through more than two of the side walls for receiving sensors for monitoring multiple parameters in the fluid.

17 Claims, 4 Drawing Sheets

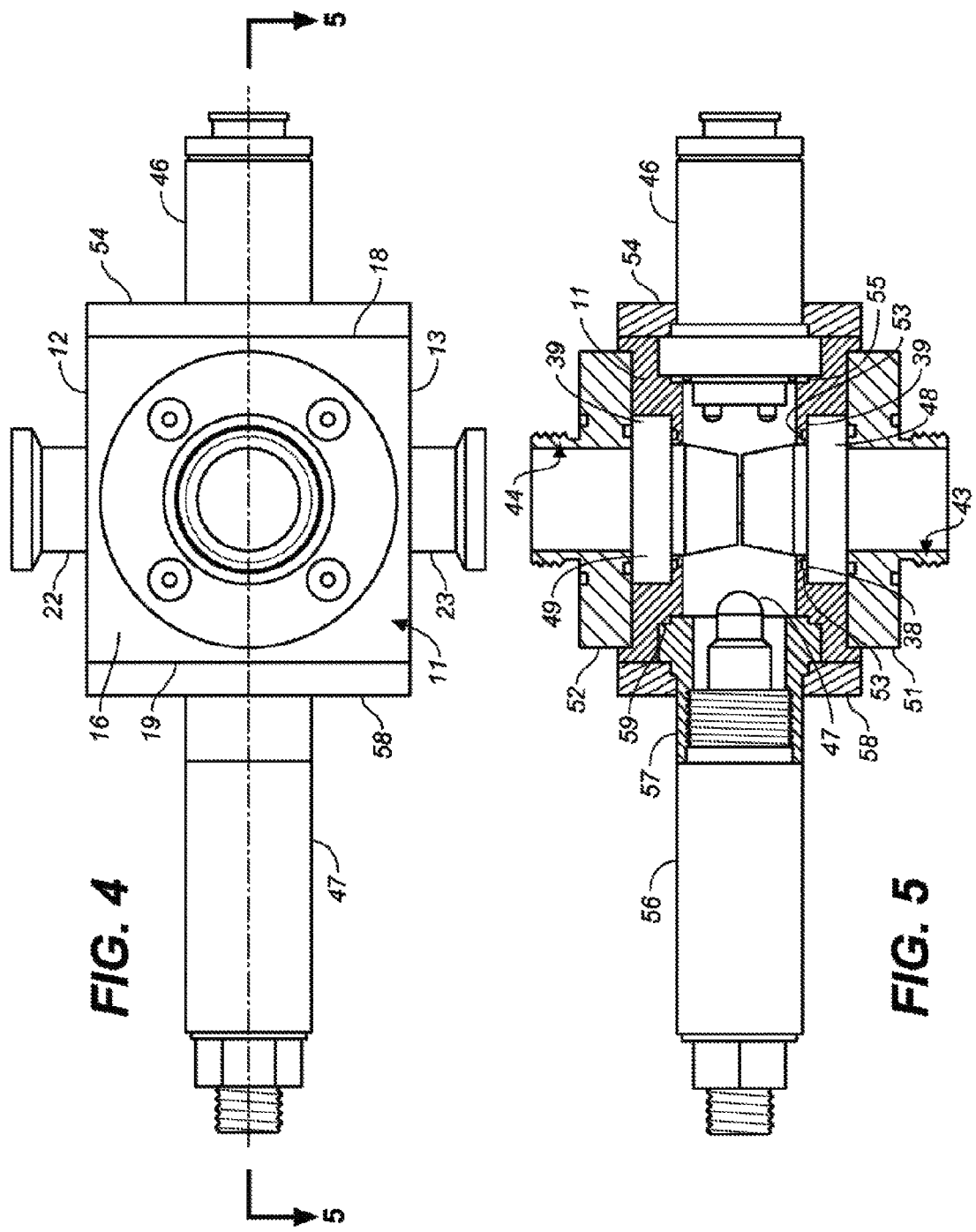

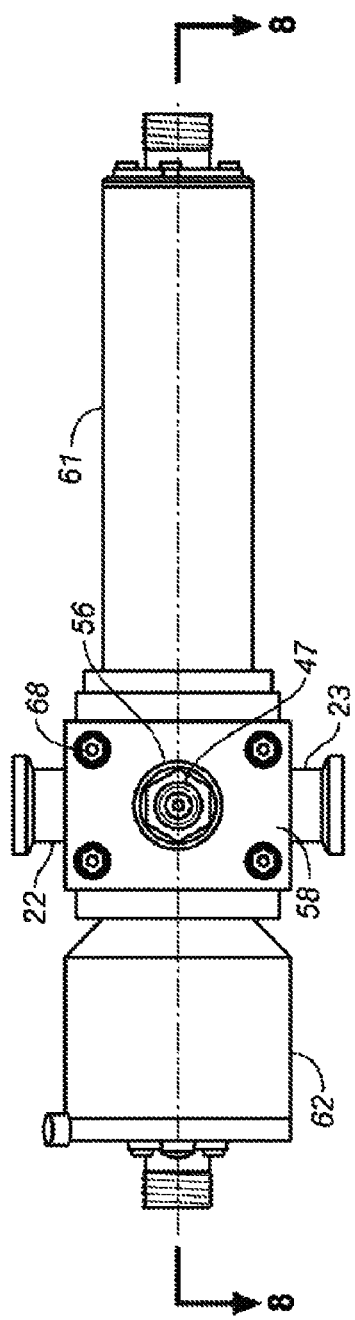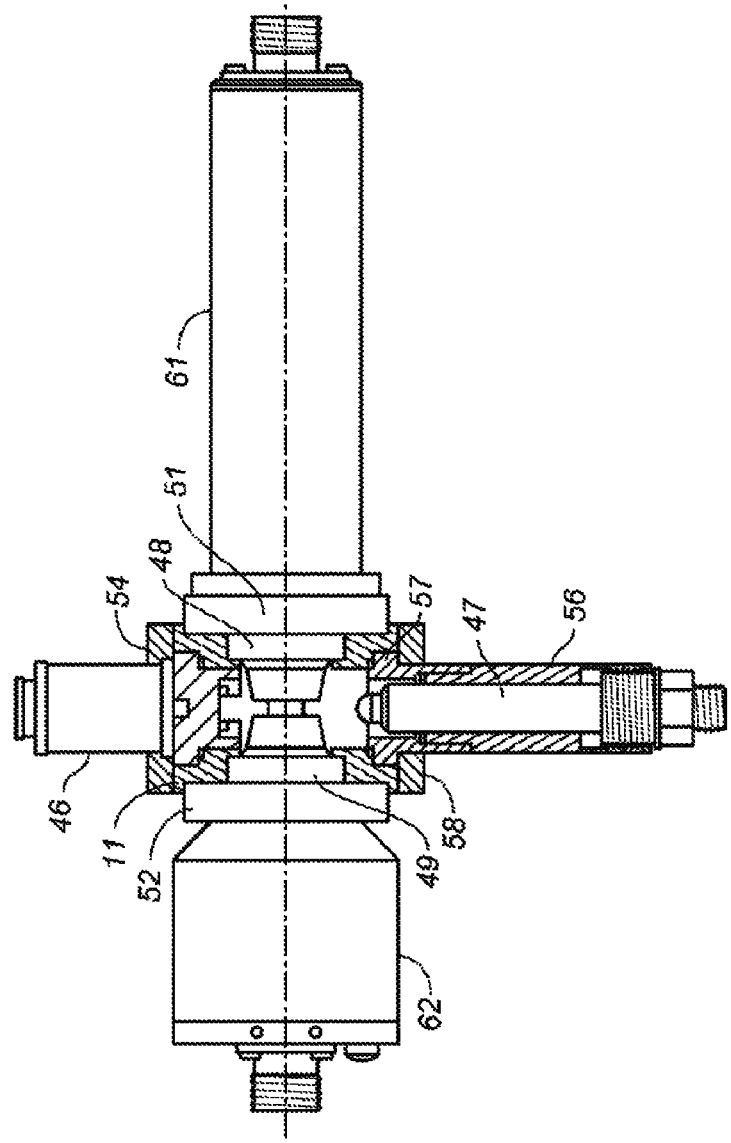

MULTI-PORT INLINE FLOW CELL FOR USE IN MONITORING MULTIPLE PARAMETERS IN A SANITARY PROCESS LINE

BACKGROUND OF THE INVENTION

1. Field of Invention

This invention pertains generally to the monitoring of parameters in sanitary process lines and, more particularly, to an inline multi-port flow cell for use in monitoring multiple parameters in a sanitary process line.

2. Related Art

Inline monitoring or measurement of parameters such as pH, oxygen, carbon dioxide, specific Ion, conductivity, temperature, and optical absorbance is commonly employed in the biotechnology and pharmaceutical industries. With processes in which multiple parameters are to be monitored, the complexity of the piping and layout of the measurement systems can be problematic, and the integrity of the system can be compromised.

Sensors for making inline measurements are typically mounted on flow cells, and when more than one parameter must be measured, multiple flow cells are required. In installations of this type, the flow cells are typically stacked.

Heretofore, optical and electro-chemical sensors have been individually placed in process lines, and if both electrochemical and optical measurements are needed on the same process line, then two or more flow cells are also required.

OBJECTS AND SUMMARY OF THE INVENTION

It is, in general, an object of the invention to provide a new and improved flow cell for use in monitoring multiple parameters in a sanitary process line.

Another object of the invention is to provide a flow cell of the above character which overcomes the limitations and disadvantages of flow cells heretofore provided.

These and other objects are achieved in accordance with the invention by providing an inline flow cell having a body with opposing end walls, a flow passageway extending along an axis between the end walls, and a plurality of side walls disposed tangentially about the axis, inlet and outlet fittings communicating with the passageway at the ends of the body for connecting the flow cell in a sanitary process line with fluid in the line flowing through the passageway, and monitoring ports opening through more than two of the side walls for receiving sensors for monitoring multiple parameters in the fluid.

BRIEF DESCRIPTION OF THE DRAWINGS

FIG. 4 is a side elevational view of the flow cell in the embodiment of FIG. 1 with sensors mounted in its monitoring ports.

FIG. 5 is a horizontal sectional view taken along line 5-5 in FIG. 4.

FIG. 7 is a side elevational view of the embodiment of FIG. 6.

FIG. 8 is a top plan view, partly broken away, of the embodiment of FIG. 6

DETAILED DESCRIPTION

Figure 1:
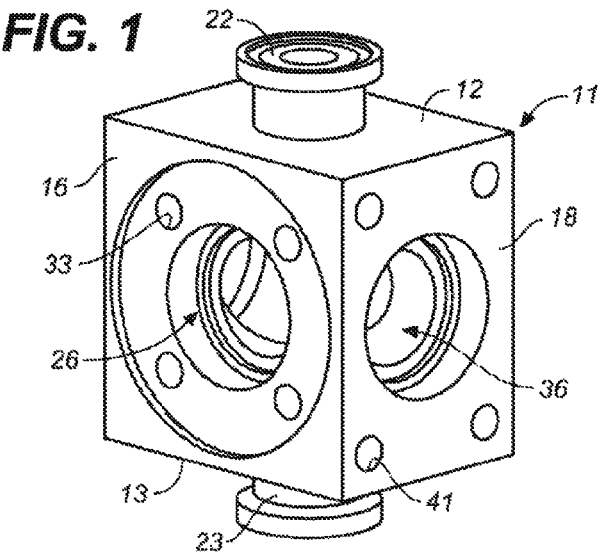
FIG. 1 is an isometric view of one embodiment of an inline multi-port flow cell for use in monitoring multiple parameters in a sanitary process line in accordance with the invention.
Figure 2:
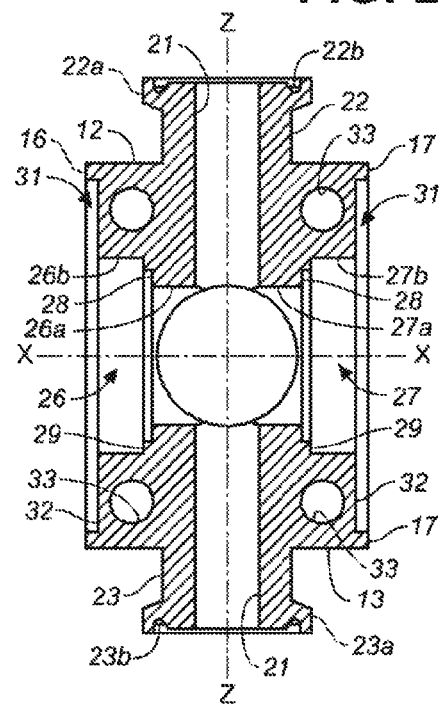
FIGS. 2 and 3 are vertical sectional views of the embodiment of FIG. 1.
Figure 3:
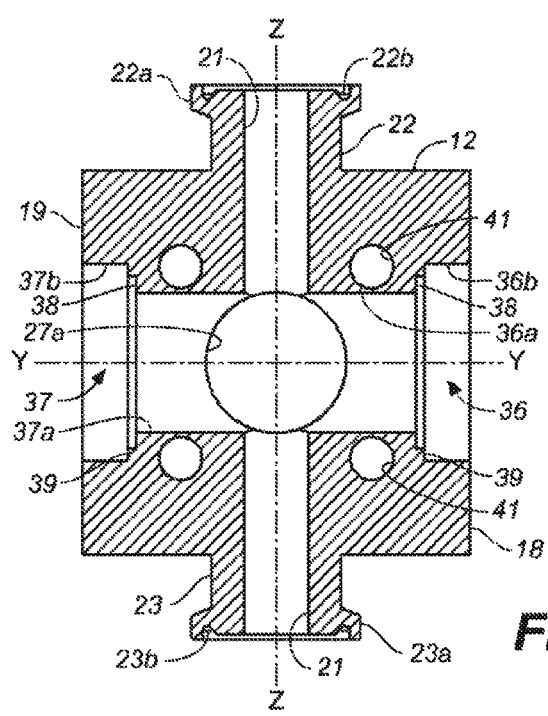

As illustrated in FIGS. 1-3, the flow cell has a generally rectangular body 11 with a top wall 12, a bottom wall 13, and side walls 16-19. In the embodiment illustrated, the top and bottom walls are generally square, and the side walls are generally rectangular, with side walls 16, 17 being narrower than side walls 18, 19. The body is preferably formed of a material which can be readily cleaned and sterilized such as stainless steel or a thermoplastic fluoropolymer such as that marketed under the Kynar trademark.

A flow passageway 21 extends along the z-axis of the body between top wall 12 and bottom wall 13, with inlet and outlet fittings 22, 23 communicating with the passageway on the upper and lower sides of the body for connecting the flow cell inline with a sanitary process line, with fluid in the line flowing through the passageway. In the embodiment illustrated, the inlet and outlet fittings are tri-clamp fittings which are formed integrally with the body and have connecting flanges 22a, 23a with O-ring grooves 22b, 23b at their outer ends. However, other suitable fittings can be utilized, if desired.

Monitoring ports 26, 27 open through side walls 16, 17 on opposite sides of the body for receiving sensors for monitoring parameters in the fluid. Each of these ports has an inner bore 26a, 27a and an outer bore 26b, 27b which extend along the x-axis of the body, with the inner bores intersecting flow passageway 21 and the outer bores opening through the side walls. The outer bores are larger in diameter than the inner bores, and a pair of annular shoulders 28, 29 are formed between the bores. Annular recesses 31 with inner or bottom walls 32 are formed at the outer ends of outer bores 26b, 27b for receiving portions of the sensors and/or the hardware with which the sensors are attached to the ports. Mounting holes 33 are spaced circumferentially about the ports and open through the outer shoulders. In a stainless steel body, the mounting holes are threaded, whereas in a Kynar body, they are unthreaded and extend all the way through the body.

Additional monitoring ports 36, 37 open through side walls 18, 19 on the remaining sides of the body for receiving additional sensors for monitoring additional parameters in the fluid. These ports are similar to ports 26, 27 and include inner bores 26a, 27a and outer bores 26b, 27b which extend along the y-axis of the body, with the inner bores intersecting the flow passageway and the outer bores opening through the side walls. The outer bores are larger in diameter than the inner bores, with annular shoulders 38, 39 between the bores. Mounting holes 41 open through side walls 18, 19 and are spaced circumferentially about outer bores 36b, 37b for use in attaching sensors to the ports. Like mounting holes 33, they are threaded In a stainless steel body and unthreaded in a Kynar body.

With the shoulders between the bores and the bottom walls of the outer recesses all facing in an outward direction, these surfaces and the walls of the bores are readily accessible for sanitization by steam or other cleaning processes without removing the cell from the process line.

In the embodiment shown in FIGS. 4 and 5, optical sensors 43, 44 are mounted in ports 26, 27, a conductivity and temperature probe 46 is mounted in port 36, and a pH probe 47 is mounted in port 37. The optical sensors include optical windows 48, 49, with retaining rings 51, 52 clamping the windows against shoulders 39 and O-rings 53 providing seals between the windows and shoulders 38 to prevent fluid from leaking between the passageway and the ports. The conductivity and temperature probe is received in the outer bore of port 36, with a retaining plate 54 clamping the sensor to the flow cell body and an O-ring 55 providing a fluid-tight seal between the probe and the body. The pH probe is mounted in a housing 56 which is received in the outer bore of port 37 and secured to the flow cell body by a retaining plate 58, with an O-ring 59 providing a fluid-tight seal between the housing and the body.

With this embodiment, it is possible to make optical measurements at the same time and in the same place that conductivity, temperature and pH are being monitored or measured.

Figure 6:
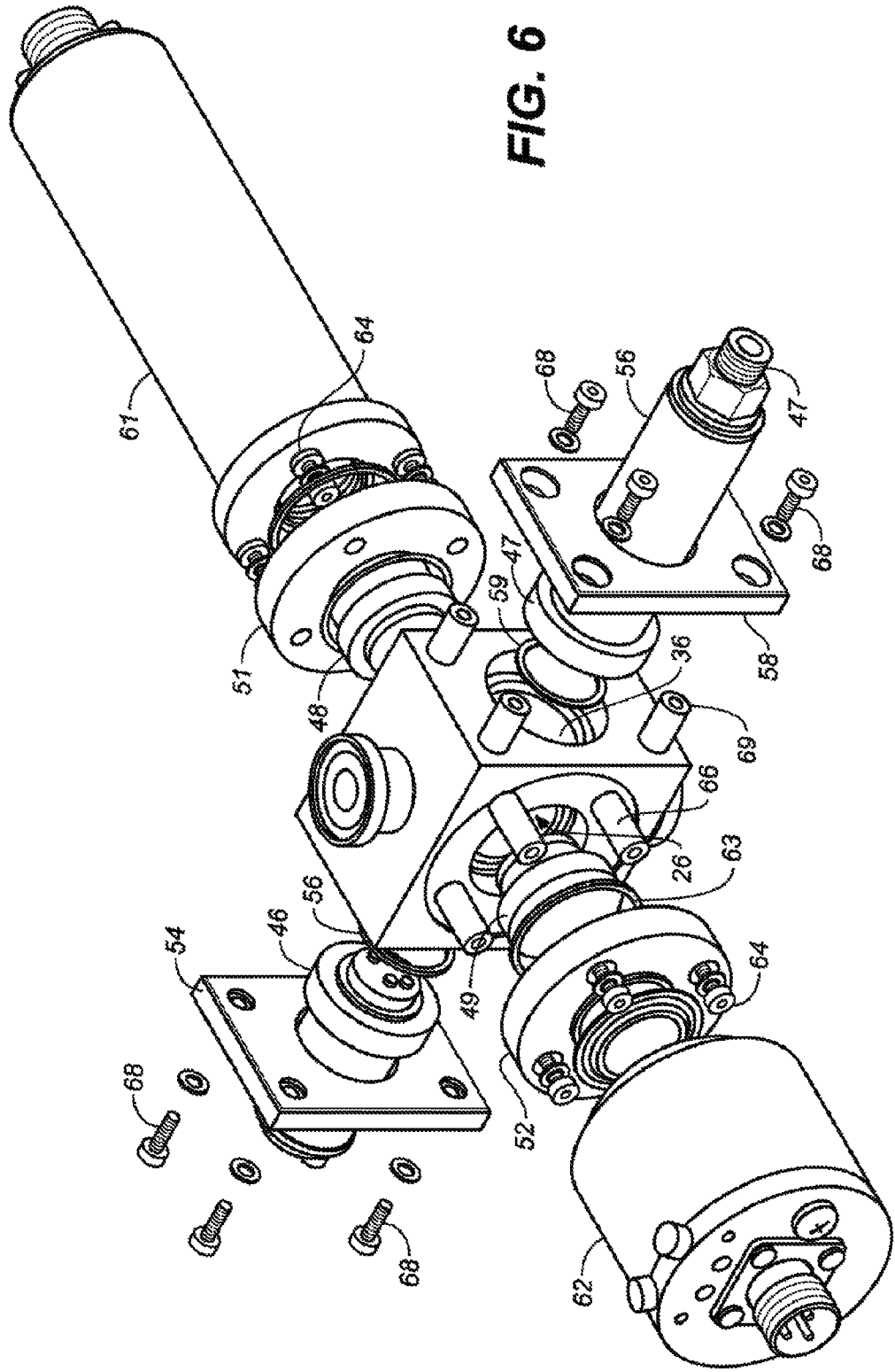
FIG. 6 is an exploded isometric view of the flow cell in the embodiment of FIG. 1 with a UV lamp assembly and detector in two of its ports, a conductivity probe in a third port, and a pH probe in a fourth port.

The embodiment illustrated in FIGS. 6-8 is similar to the embodiment of FIGS. 4 and 5, with like reference numerals designating corresponding elements in the two embodiments. In this embodiment, an ultraviolet lamp assembly 61 is mounted on retaining ring 51 for directing UV light through the optical window 49 in port 27, and a UV detector 62 is mounted on retaining ring 52 for receiving UV radiation through optical window 48 in port 26, with O-rings 63 providing seals between the retaining rings and the windows. With the Kynar body illustrated, the retaining rings are secured to the flow cell body by mounting screws 64 which are threaded into the opposing ends of stainless steel dowel rods 66 that extend through the body in mounting holes 33. With a stainless steel body, the mounting screws can be threaded directly into the mounting holes, and the dowel rods are not required.

In this embodiment, pH probe assembly 56 is mounted in port 36, and conductivity probe 46 is mounted in port 37, with retaining plates 54, 58 being affixed to the flow cell body by mounting screws 68 threaded into the opposing ends dowel rods 69 which extend through the body in mounting holes 41. With a stainless steel body, the mounting screws would be threaded directly into the mounting holes. As in the embodiment of FIGS. 4-5, optical parameters can be monitored or measured simultaneously with pH and conductivity.

The invention has a number of important features and advantages. It permits multiple parameters to be monitored or measured simultaneously at a single point in a sanitary process line. With fewer flow cells and measuring points, there is less hold-up space in the line, and both installation and instrumentation are simplified. Moreover, when interdependent process variables are measured at one point, the measurements are synchronized. Cost is reduced by integrating multiple measurements at one point, and sanitation of a process line is also easier with fewer monitoring or measuring points in the line.

It is apparent from the foregoing that a new and improved flow cell for use in monitoring multiple parameters in a sanitary process line has been provided. While only certain presently preferred embodiments have been described in detail, as will be apparent to those familiar with the art, certain changes and modifications can be made without departing from the scope of the invention as defined by the following claims.

The invention claimed is:

1. An inline flow cell for use in monitoring multiple parameters in a sanitary process line, comprising: a body having opposing end walls, a flow passageway extending along an axis between the end walls, and a plurality of side walls disposed tangentially about the axis, inlet and outlet fittings communicating with the passageway at the ends of the body for connecting the flow cell in a sanitary process line with fluid in the line flowing through the passageway, and monitoring ports opening through more than two of the side walls for receiving sensors for monitoring multiple parameters in the fluid.

2. The flow cell of claim 1 wherein each of the ports has an inner bore adjacent to the passageway and an outer bore of larger diameter than the inner bore toward the outer side of the body, with an outwardly facing annular seat at the junction of the inner and outer bores which is readily accessible for cleaning when the sensor is removed from the port.

3. The flow cell of claim 1 including an optical window which is mounted in at least one of the ports and sealed to the body to prevent fluid in the passageway from entering the port.

4. The flow cell of claim 1 wherein the body is fabricated of stainless steel.

5. The flow cell of claim 1 wherein the body is fabricated of a thermoplastic fluoropolymer.

6. An inline flow cell for use in monitoring multiple parameters in a sanitary process line, comprising: a body having an axially extending flow passageway formed therein, inlet and outlet fittings communicating with the passageway on opposite sides of the body for connecting the flow cell in a sanitary process line with fluid in the line flowing through the passageway, first and second monitoring ports opening through first and second sides of the body and communicating with the passageway for receiving sensors for monitoring at least one parameter in the fluid, and third and fourth monitoring ports opening through third and fourth sides of the body and communicating with the passageway for receiving additional sensors for monitoring at least one additional parameter in the fluid.

7. The flow cell of claim 6 wherein each of the ports has an inner bore adjacent to the passageway and an outer bore of larger diameter than the inner bore toward the outer side of the body, with an outwardly facing annular seat at the junction of the inner and outer bores which is readily accessible for cleaning when the sensor is removed from the port.

8. The flow cell of claim 6 wherein the first and second ports are disposed on first and second opposite sides of the passageway, and the third and fourth ports are disposed on third and fourth opposite sides of the passageway.

9. The flow cell of claim 6 wherein the sides of the body through which the ports open are disposed tangentially about the axis of the passageway.

10. The flow cell of claim 6 including an optical window which is mounted in at least one of the ports and sealed to the body to prevent fluid in the passageway from entering the port.

11. The flow cell of claim 6 wherein the body is fabricated of stainless steel.

12. The flow cell of claim 6 wherein the body is fabricated of a thermoplastic fluoropolymer.

13. An inline flow cell for use in monitoring multiple parameters in a sanitary process line, comprising: a generally rectangular body having opposing end walls, a flow passageway extending along an axis between the end walls, and four side walls disposed in quadrature about the axis, inlet and outlet fittings communicating with the passageway at the ends of the body for connecting the flow cell in a sanitary process line with fluid in the line flowing through the passageway, and monitoring ports opening through the four side walls for receiving sensors for monitoring multiple parameters in the fluid.

14. The flow cell of claim 13 wherein each of the ports has an inner bore adjacent to the passageway and an outer bore of larger diameter than the inner bore toward the outer side of the body, with an outwardly facing annular seat at the junction of the inner and outer bores which is readily accessible for cleaning when the sensor is removed from the port.

15. The flow cell of claim 13 including an optical window which is mounted in at least one of the ports and sealed to the body to prevent fluid in the passageway from entering the port.

16. The flow cell of claim 13 wherein the body is fabricated of stainless steel.

17. The flow cell of claim 13 wherein the body is fabricated of a thermoplastic fluoropolymer.

* * * * *